US007687530B2

(12) United States Patent
Williams

(10) Patent No.: US 7,687,530 B2
(45) Date of Patent: *Mar. 30, 2010

(54) INHIBITION OF CHRONIC TISSUE TRANSPLANT REJECTION

(75) Inventor: John M. Williams, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 301 days.

This patent is subject to a terminal disclaimer.

(21) Appl. No.: 10/719,055

(22) Filed: Nov. 21, 2003

(65) Prior Publication Data

US 2004/0163654 A1 Aug. 26, 2004

Related U.S. Application Data

(60) Provisional application No. 60/428,332, filed on Nov. 21, 2002.

(51) Int. Cl.
*A01N 43/50* (2006.01)
*A61K 31/16* (2006.01)
(52) U.S. Cl. ..................... 514/399; 514/613
(58) Field of Classification Search ............... 514/399, 514/613
See application file for complete search history.

(56) References Cited

U.S. PATENT DOCUMENTS

| | | | |
|---|---|---|---|
| 5,540,931 | A | 7/1996 | Hewitt et al. |
| 5,654,312 | A | 8/1997 | Andrulis, Jr. et al. |
| 5,795,967 | A | 8/1998 | Aggarwal et al. |
| 5,801,193 | A | 9/1998 | Ojo-Amaize et al. |
| 5,958,413 | A | 9/1999 | Anagnostopulos et al. |
| 5,990,103 | A | 11/1999 | Schonharting et al. |
| 6,020,323 | A | 2/2000 | Cohen et al. |
| 6,030,615 | A | 2/2000 | Bucala et al. |
| 6,204,245 | B1 | 3/2001 | Siegel et al. |
| 6,211,160 | B1 | 4/2001 | Wilson et al. |
| 6,235,281 | B1 | 5/2001 | Stenzel et al. |
| 6,270,766 | B1 | 8/2001 | Feldman et al. |
| 6,294,170 | B1 | 9/2001 | Boone et al. |
| 6,299,878 | B1 | 10/2001 | Pierpadi et al. |
| 6,306,820 | B1 | 10/2001 | Bendele et al. |
| 6,331,560 | B1 | 12/2001 | Shohami et al. |
| 6,337,325 | B1 | 1/2002 | Schonharting et al. |
| 6,376,665 | B1 | 4/2002 | Duan et al. |
| 6,407,218 | B1 | 6/2002 | Tamarkin et al. |
| 6,420,374 | B1 | 7/2002 | Bianco et al. |
| 6,432,962 | B2 | 8/2002 | Horneman |
| 6,432,968 | B1 | 8/2002 | Schonharting et al. |
| 6,503,184 | B1 | 1/2003 | Ni et al. |
| 6,506,569 | B1 | 1/2003 | Ni et al. |
| 6,509,015 | B1 | 1/2003 | Salfeld et al. |
| 2002/0119988 | A1 | 8/2002 | Sneddon et al. |
| 2004/0072728 | A1 | 4/2004 | Fawwaz |

FOREIGN PATENT DOCUMENTS

| | | |
|---|---|---|
| EP | 0 401 747 A | 12/1990 |
| WO | WO 94/08619 | 4/1994 |
| WO | WO 95/09652 | 4/1995 |
| WO | WO 98/39026 | 9/1998 |
| WO | WO 01/34649 | 5/2001 |
| WO | WO 01/87849 | 11/2001 |
| WO | WO 01/87849 A2 * | 11/2001 |

OTHER PUBLICATIONS

Sviland et al J. Clin. Pathology 1999, 52:910-913.*
Jamieson et al. (Transplant Int. (1991) 4:67-71).*
Minor Histocompatibility Antigens in GVHD & Graft Rejection, NIH Guide, vol. 26, No. 24, Jul. 25, 1997, 7 pages.*
Yuan, X. et al., "A novel CD154 monoclonal antibody in acute and chronic rat vascularized cardiac allograft rejection," *Transplantation* 73(11):1736-1742 (2002).
Turner, D. M., et al., "A Genetic Marker of High TNF-α Production in Heart Transplant Recipients," *Transplantation*, 60(10):1113-1117 (1995).
Couriel, D., et al., "TNF-Alpha Inhibition for the Treatment of Chronic GVHD," *Blood*, 100(11):847a (2002) Abstract.
Hancock, W. W., et al., "Costimulatory function and expression of CD40 ligand, CD80, and CD86 in vascularized murine cardiac allograft rejection," *Proc. Natl. Acad. Sci. USA*.93:13967-13972 (1996).
Retrieved from internet, www4.od.nih.gov/biomarkers/b9.htm, Cytokine Gene Polymorphisms, pp. 4 and 5, Jul. 31, 2007.
Chalasani, Geetha, et al., "The Allograft Defines the Type of Rejection (Acute versus Chronic) in the Face of an Established Effector Immune Response," The Journal of Immunology, 172: 7813-7820 (2004).

(Continued)

*Primary Examiner*—Michael G Hartley
*Assistant Examiner*—Shirley V Gembeh
(74) *Attorney, Agent, or Firm*—Hamilton, Brook, Smith & Reynolds, P.C.

(57) ABSTRACT

Disclosed is a method of inhibiting acute and chronic tissue transplant rejection in a subject with a tissue transplant. The method comprises the step of administering to the subject an effective amount of a compound represented by Formula (I):

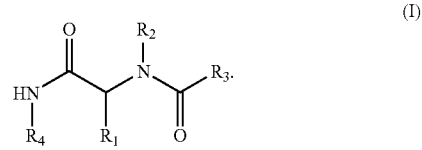

The values of the variables in Formula (I) are described herein.

1 Claim, 2 Drawing Sheets

OTHER PUBLICATIONS

Goodman, J. and Mohanakumar T., "Chronic rejection: failure of immune regulation," *Front. BioSci.*, Sep. 1;8:s838-44 (2003).

Kunkel, S.L. et al., "The Role of TNF in Diverse Pathologic Processes," *Biotherapy*, 3:135-141 (Apr. 1991).

Heidenreich, S., et al,, "Monocyte Activation for Enhanced Tumour Necrosis Factor-$\alpha$ and Interleukin 6 Production During Chronic Renal Allograft Rejection," *Transplant Immunology*, 2:35-40 (1994).

* cited by examiner

INHIBITION OF CHRONIC TISSUE TRANSPLANT REJECTION

RELATED APPLICATIONS PARAGRAPH

This Application claims the benefit of U.S. Provisional Application No. 60/428,332, filed Nov. 21, 2002, the entire teachings of which are incorporated herein by reference.

BACKGROUND OF THE INVENTION

There have been improvements in the management of acute transplant rejection over the last thirty years as seen in the increased survival of transplants during the first year following the procedure. However, the half-life for long term organ survival has not improved and only about 50% of the transplants are functional at ten years. Chronic transplant rejection, as opposed to acute transplant rejection, is the cause for the majority of transplant failures.

Acute transplant rejection occurs as a result of the immune system of the transplant recipient attacking the transplanted tissue. Acute rejection is rapid, generally occurs within hours to weeks after transplant of the tissue and can typically be suppressed with the use of immunosuppressive drugs such as cyclosporin A. Whereas acute rejection is suppressed with immunosuppressive protocols, treatment for chronic rejection is less well defined. Acute rejection and chronic rejection have significantly different characteristics as immune responses. For example, chronic rejection occurs over time, typically several months to years after engraftment, even in the presence of successful immunosuppression. It involves multiple factors and processes of the host and is usually the result of a prolonged process of wound healing the host undergoes post-transplant. Therefore, chronic rejection is not totally immunological in origin and additional causes(s) are not fully understood. They may include ischemic insult, denervation of the transplanted tissue, hyperlipidemia and hypertension associated with immunosuppressive drugs.

For most organs, the most definitive way of showing that rejection is occurring is by biopsy of that organ. For practical reasons, however, biopsies are not always done and are particularly less practical when chronic rejection is suspected. Chronic rejection of a transplant organ is generally characterized as failure of the organ after it has begun to perform its function in the recipient or host. Thus, chronic rejection is commonly monitored by a decrease in organ function which, if unarrested, results in failure of the organ, infection, and necrosis of organ tissue. Chronic rejection is identified, commonly too late for treatment that can save the transplant, by pathogenic fibrosis, which is characterized by extensive deposition of the extracellular matrix proteins: collagen, fibronectin, and elastin, and by emergence of cells with the myofibroblast phenotype. Fibrosis becomes a telltale characteristic of chronic rejection where fibrogenesis is observed to damage organ microstructures or to block passages that need to remain open for organ function.

The chronic rejection process is not inhibited by any known therapeutic regimen at this time. Moreover, as noted above, it is sometimes difficult to detect and treat in a time frame that will save the transplant. Thus, additional improvements in the long-term survival of organ transplant patients are dependent on the development of new techniques for managing chronic transplant rejection.

SUMMARY OF THE INVENTION

A new class of compounds that is effective in inhibiting chronic transplant rejection has now been discovered and is disclosed herein. In one example, the histopathological evidence of chronic rejection was inhibited in two mouse models by Compound 1, shown below. In the first model, chronic rejection of fully MHC class II mismatched transplanted hearts in recipient mice at eight weeks post surgery was inhibited by treatment with 75 mg/kg/day of

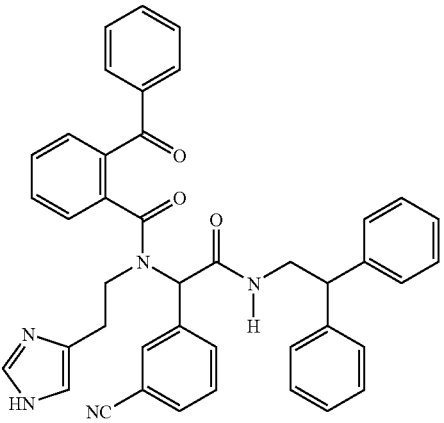

Compound 1

Compound 1 alone during the two weeks following surgery. In the second model, chronic rejection of fully MHC class II mismatched transplanted hearts in recipient mice at 120 days post surgery was inhibited when treatment with 75 mg/kg/day of Compound 1 during the two weeks following surgery was combined with a single administration of 250 μg of anti-CD154 monoclonal antibody immediately following transplant surgery. Treatment with anti-CD154 monoclonal antibody alone suppresses acute rejection, but is ineffective in preventing chronic rejection of transplanted tissue. Based on these results, methods of treating chronic transplant rejection are disclosed herein.

The present invention is a method of inhibiting tissue transplant rejection in a subject with a tissue transplant. The method is effective against both acute and chronic rejection of transplanted tissue, but is particularly advantageous in inhibiting chronic transplant rejection. The method comprises the step of administering to the subject an effective amount of a compound represented by Formula (I):

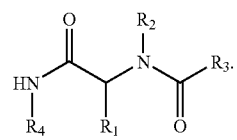

(I)

$R_1$ is a substituted or unsubstituted aryl group or a substituted or unsubstituted alkyl group.

$R_2$ is an optionally substituted aralkyl group or an alkyl group substituted with —$NR_5R_6$.

$R_3$ is a substituted or unsubstituted alkyl group or a substituted or unsubstituted aryl group.

$R_4$ a substituted or unsubstituted alkyl group or a substituted or unsubstituted aryl group.

$R_5$ and $R_6$ are independently selected from a substituted or unsubstituted alkyl group or a substituted or unsubstituted aryl group or $R_5$ and $R_6$ taken together with the nitrogen to which they are attached are a non-aromatic heterocyclic group.

The disclosed method can be advantageously used to treat chronic rejection of transplanted tissue, a condition for which heretofore effective treatments were unavailable. Additionally, acute rejection of transplanted tissue can also be inhibited with the disclosed method.

DETAILED DESCRIPTION OF THE INVENTION

Figure 1:
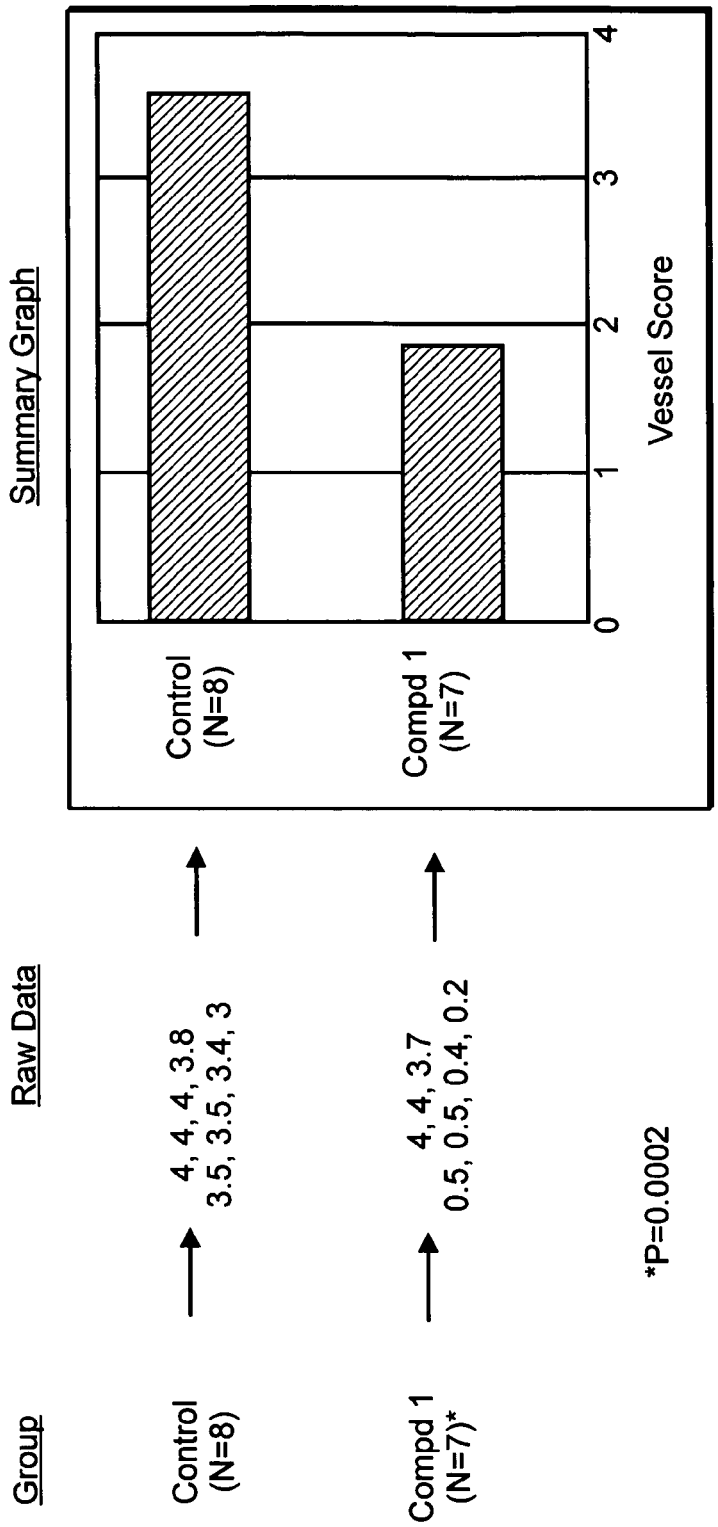
FIG. 1 is a graph showing inhibition of chronic vasculopathy in transplanted hearts in a model consisting of only MHC class II mismatched mice at eight weeks following heart transplant. The graph compares inhibition of chronic vasculopathy in a group of mice treated with 75 mg/kg of Compound 1 subcutaneously for fourteen days after heart transplant surgery with an untreated control group. The scores shown in the graph range from zero to five to indicate the severity of chronic rejection accelerated atherosclerosis, with zero being normal blood vessel and five being fully occluded.

Disclosed herein is a method of treating (preventing, inhibiting or suppressing) rejection of transplanted tissue in a recipient subject. The method is particularly effective in treating (preventing, inhibiting or suppressing) chronic transplant rejection. Optionally, the disclosed method can also be used to treat (prevent, inhibit or suppress) acute transplant rejection.

"Acute transplant rejection" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

The term "transplant rejection" encompasses both acute and chronic transplant rejection.

As described above, the disclosed methods can be advantageously used to inhibit or suppress transplant rejection, preferably chronic rejection, in a mammal with an organ or tissue transplant. The most common type of transplant is an allograft, which is a graft between members of the same species.

In one alternative, the transplanted tissue or organ is bio-engineered, e.g., when the transplanted tissue or organ is grown from a stem cell or other type of precursor cell(s). Bio-engineered tissues or organs can be grown outside of the body and transplanted directly into the host. Alternatively, the precursor cells or immature organ or tissue is transplanted into the host to grow and mature.

The disclosed method can also be used to treat tranplant rejection when the tranplanted organ or tissue is a xenograft, i.e., the donor is a member of a species different than the recipient. Xenografts are advantageously used with a bio-engineered tissue or organ, which, instead of being transplanted directly into the recipient in need of the tissue or organ, can be transplanted into a surrogate host such as non-human mammal until a suitable human recipient in need of the bio-engineered tissue or organ is identified. Alternatively, the tissue or organ can be transplanted into the surrogate to allow the bio-engineered tissue or organ to mature. Use of surrogate hosts may be preferred in instances where further development of the tissue or organ is required before transplantation into a human recipient. In another alternative, a xenograft is used when a suitable allograft donor is unavailable. When transplanting into a different a species, it is desirable to select a host such that the size of the organs in the host and donor are similar. In addition, the host is selected to minimize transmission of communicable diseases.

The term "aryl group", (e.g., the aryl groups represented by $R_1$, $R_3$ and $R_4$) used alone or as part of a larger moiety such as "aralkyl" (e.g., the aralkyl group represented by $R_2$), refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, and tetrazolyl.

The term "aryl group", used alone or as part of a larger moiety such as "aralkyl", also includes fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, quinoxalinyl, quinazolinyl, benzoisothiazolyl, benzooxazolyl, benzoisooxazolyl, benzimidazolyl, quinolinyl, isoquinolinyl and isoindolyl.

The term "aryl group", used alone or as part of a larger moiety such as "aralkyl", also includes carbocyclic aromatic rings or heteroaryl aromatic rings fused to a cycloalkyl group or an non-aromatic heterocyclic group. Examples include indanyl, tetrahydronaphthyl and fluorenyl.

The term "alkyl group" (e.g., the alkyl groups represented by $R_1$-$R_6$), used alone or as part of a larger moiety such as "aralkyl" (e.g., the aralkyl group represented by $R_2$) or "cycloalkylalkyl", is a straight, branched or cyclic non-aromatic hydrocarbon which is completely saturated. Typically, a straight or branched alkyl group has from 1 to about 10 carbon atoms, preferably from 1 to about 4, and a cyclic aliphatic group has from 3 to about 10 carbon atoms, preferably from 3 to about 8. Examples of suitable straight or branched alkyl group include methyl, ethyl, n-propyl, iso-propyl, n-butyl, sec-butyl, tert-butyl, pentyl, hexyl, heptyl or octyl; and examples of suitable cycloalkyl groups include cyclopropyl, cyclobutyl, cyclopentyl, cyclohexyl, cycloheptyl and cyclooctyl. A C1-C10 straight or branched alkyl group or a C3-C8 cyclic alkyl group are also referred to as a "lower alkyl" group.

An "aralkyl group" is an alkyl group substituted with one or more aryl groups. A "substituted aralkyl group" can have one or more substituents on the alkyl part of the aralkyl group and/or on the aryl part of the aralkyl group. Suitable aralkyl group substituents are described below in the section providing examples of aryl group substituents and alkyl group substituents.

A "heteroaralkyl group" is an alkyl group substituted with one or more heteroaryl groups. A "substituted heteroaralkyl group" can have one or more substituents on the alkyl part of the heteroaralkyl group and/or on the heteroaryl part of the heteroaralkyl group. Suitable heteroaralkyl group substituents are described below in the section providing examples of aryl group substituents and alkyl group substituents.

A "cycloalkylalkyl group" is an alkyl group substituted with one or more cycloalkyl groups. A "substituted cycloalkylalkyl group" can have one or more substituents on the alkyl part or cycloalkylalkyl part of the cycloalkylalkyl group. Suitable cycloalkylalkyl group substituents are described below in the section providing examples of alkyl group substituents.

A "heterocycloalkylalkyl group" is an alkyl group substituted with one or more non-aromatic heterocyclic groups. A "substituted heterocycloalkylalkyl group" can have one or more substituents on the alkyl part or non-aromatic heterocyclic part of the heterocycloalkylalkyl group. Suitable heterocycloalkylalkyl group substituents are described below in the section providing examples of alkyl group substituents and non-aromatic heterocyclic group substitutents.

The term "non-aromatic heterocyclic ring" (e.g., non-aromatic heterocyclic groups represented by —$NR_5R_6$) refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl.

Suitable substituents for an alkyl group, for a carbon atom on an aryl group or a non-aromatic heterocyclic group are those which do not substantially interfere with the ability of the compound to inhibit transplant rejection. Examples of suitable substituents for a carbon atom of an aryl, alkyl or a carbon atom of a non-aromatic heterocyclic group include —OH, halogen (—Br, —Cl, —I and —F), R, —$CH_2$R, —$OCH_2$R, —$CH_2$OC(O)R, —OR, —O—COR, —COR, —CN, —$NO_2$, —COOH, —$SO_3$H, —$NH_2$, —NHR, —N(R)$_2$, —COOR, —CHO, —$CONH_2$, —CONHR, —CON(R)$_2$, —NHCOR, —NRCOR, —$NHCONH_2$, —NHCONRH, —CONRH, —NHCON(R)$_2$, —$NRCONH_2$, —NRCONRH, —NRCON(R)$_2$, —C(=NH)—$NH_2$, —C(=NH)—NHR, —C(=NH)—N(R)$_2$, —C(=NR)—$NH_2$, —C(=NR)—NHR, —C(=NR)—N(R)$_2$, —NH—C(=NH)—$NH_2$, —NH—C(=NH)—NHR, —NH—C(=NH)—N(R)$_2$, —NH—C(=NR)—$NH_2$, —NH—C(=NR)—NHR, —NH—C(=NR)—N(R)$_2$, —NRH—C(=NH)—$NH_2$, —NR—C(=NH)—NHR, —NR—C(=NH)—N(R)$_2$, —NR—C(=NR)—$NH_2$, —NR—C(=NR)—NHR, —NR—C(=NR)—N(R)$_2$, —$SO_2NH_2$, —$SO_2$NHR, —$SO_2NR_2$, —SH, —$SO_k$R (k is 0, 1 or 2) and —NH—C(=NH)—$NH_2$. Each R is independently an alkyl, substituted alkyl, benzyl, substituted benzyl, aryl or substituted aryl group. Preferably, R is an alkyl, benzylic or aryl group. In addition, —N(R)$_2$, taken together, can also form a substituted or unsubstituted non-aromatic heterocyclic group, such as pyrollidinyl, piperidinyl, morpholinyl and thiomorpholinyl. Examples of substituents on the alkyl, aryl or benzyl group represented by R include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. A substituted aryl, alkyl and non-aromatic heterocyclic group can have more than one substitutent.

Suitable substituents on a substitutable nitrogen of a non-aromatic heterocyclic group or heteroaryl group include —R', —N(R')$_2$, —C(O)R', —$CO_2$R', —C(O)C(O)R', —C(O)$CH_2$C(O)R', —$SO_2$R', —$SO_2$N(R')$_2$, —C(=S)N(R')$_2$, —C(=NH)—N(R')$_2$, and —NR'$SO_2$R'; wherein R' is hydrogen, an alkyl group, a substituted alkyl group, phenyl (Ph), substituted Ph, —O(Ph), substituted —O(Ph), $CH_2$(Ph), or an unsubstituted heteroaryl or non-aromatic heterocyclic ring. Examples of substituents on the aliphatic group or the phenyl ring represented by R' include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

Additionally, pharmaceutically acceptable salts of the disclosed compounds can be used in the disclosed methods. For example, an acid salt of a compound containing an amine or other basic group can be obtained, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

An "effective amount" according to the present invention of a compound of Formula (I) is the quantity which, when administered to a transplant recipient, inhibits or suppresses transplant rejection, i.e., delays the onset of and/or reduces the severity of one or more of the symptoms associated with transplant rejection, and preferably with chronic transplant rejection. The amount of the disclosed compound to be administered to a transplant recipient will depend on the type of transplant, the characteristics of the subject, such as general health, age, sex, body weight and tolerance to drugs. The skilled artisan will be able to determine appropriate dosages depending on these and other factors. Effective amounts of the disclosed compounds typically range between about 0.01 mg/kg per day and about 100 mg/kg per day, and preferably between 0.1 mg/kg per day and about 10 mg/kg/day.

A "subject" is a mammal, preferably a human, but can also be an animal who has received a tissue transplant and is in need of treatment to inhibit transplant rejection, and preferably chronic transplant rejection. Examples of recipient animals in need of such treatment include, e.g., companion animals (e.g., dogs, cats, and the like), farm animals (e.g., cows, sheep, pigs, horses, and the like) and laboratory animals (e.g., rats, mice, guinea pigs, and the like).

The use of the disclosed compounds to inhibit transplant rejection, e.g., chronic transplant rejection, is not limited to any particular organ or tissue type. The disclosed treatment is effective, but not limited to, inhibiting rejection of transplanted heart, kidney, lung, liver, pancreas, pancreatic islets, brain tissue, stomach, large intestine, small intestine, cornea, skin, trachea, bone, bone marrow, muscle, bladder or parts thereof.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

For oral administration, the disclosed compounds or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parental administration of the disclosed compounds, or salts thereof, can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition to the formulations described previously, the compounds may also be formulated as a depot preparation. Suitable formulations of this type include biocompatible and biodegradable polymeric hydrogel formulations using crosslinked or water insoluble polysaccharide formulations. Also included are polymerizable polyethylene oxide formulations. Formulations of this type are disclosed in U.S. Pat. Nos. 5,410,016, 4,713,448, 4,636,524, 6,083,524, 5,785,993, 4,937,270 and 5,017,229, the entire teachings of which are incorporated herein by reference. Such long acting formulations may be administered by implantation, for example, subcutaneously or intramuscularly or by intramuscular injection. Preferably, they are implanted in the microenvironment of the transplanted organ or tissue. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

Preferably disclosed compounds or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Formula I or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

The compound used in the method of the present invention can be advantageously co-administered with immunosuppressive drugs. Examples include corticosteroids, cyclosporin A, rapamycin and FK506 or antibody therapies such as anti T-cell antibodies. It is particularly useful to co-administer a compound represented by Formula (I) with rapamycin or anti-CD40L monoclonal antibody.

Compounds of the present invention can be prepared according to procedures disclosed in WO 01/87849, the entire teachings of which are incorporated herein by reference.

In a preferred embodiment, the variables for the compound represented by Formula (I) are as provided above, provided that the compound is characterized by one or more of the following features:

a) $R_1$ is an optionally substituted aryl group or an optionally substituted $C_1$-$C_4$ aralkyl group.

b) $R_1$ is an optionally substituted phenyl group or an optionally substituted phenyl-$C_1$-$C_4$ alkyl group. Preferred substituents for these values of $R_1$ include $C_1$-$C_4$ alkyl, $C_1$-$C_4$ alkoxy, halogen, CN, $C_1$-$C_4$-alkylthiol, $C_1$-$C_4$-haloalkyl and phenoxy.

c) $R_2$ is an optionally substituted heteroaralkyl group or an alkyl group substituted with —$NR_5R_6$.

d) $R_2$ is an optionally substituted imadazolyl-$C_1$-$C_4$-alkyl group or a $C_1$-$C_4$ alkyl group substituted with —$NR_5R_6$.

e) $R_2$ is an optionally substituted 2-(imidazol-4-yl)ethyl, an optionally substituted 3-(imidazol-4-yl)propyl, an optionally substituted 3-(imidazol-1-yl)propyl, an optionally substituted 2-(morpholin-4-yl)ethyl, an optionally substituted 2-(4-pyrazolyl)ethyl, an optionally substituted 2-N,N-dimethylaminoethyl or an optionally substituted 3-N,N-dimethylaminopropyl. Preferably, $R_2$ is 2-(imidazol-4-yl)ethyl.

f) $R_3$ is an optionally substituted aryl group or an optionally substituted $C_1$-$C_4$ aralkyl group.

g) $R_3$ is an optionally substituted an optionally substituted 2-cyclohexylethyl, an optionally substituted 2-cyclopentylethyl, or an optionally substituted $C_3$-$C_8$ secondary or tertiary alkyl group.

h) $R_3$ is an optionally substituted phenyl, an optionally substituted phenyl-$C_1$-$C_4$-alkyl, an optionally substituted diphenyl-$C_1$-$C_4$-alkyl, an optionally substituted pyrazolyl, an optionally substituted pyrazolyl-$C_1$-$C_4$-alkyl, an optionally substituted indolyl, an optionally substituted indolyl-$C_1$-$C_4$-alkyl, thienylphenyl, thienylphenyl-$C_1$-$C_4$-alkyl, furanylphenyl, furanylphenyl-$C_1$-$C_4$-alkyl, an optionally substituted fluorenyl, an optionally substituted fluorenyl-$C_1$-$C_4$-alkyl, an optionally substituted naphthyl, an optionally substituted naphthyl-$C_1$-$C_4$-alkyl, an optionally substituted quinoxalinyl, an optionally substituted quinoxalinyl-$C_1$-$C_4$-alkyl, an optionally substituted quinazolinyl, an optionally substituted quinazolinyl-$C_1$-$C_4$-alkyl, an optionally substituted pyrolyl, an optionally substituted pyrolyl-$C_1$-$C_4$-alkyl, an optionally substituted thienyl, an optionally substituted thienyl-$C_1$-$C_4$-alkyl, an optionally substituted furanyl, an optionally substituted furanyl-$C_1$-$C_4$-alkyl, an optionally substituted pyridyl or an optionally substituted-$C_1$-$C_4$ pyridyl.

i) $R_3$ is represented by Formula (II):

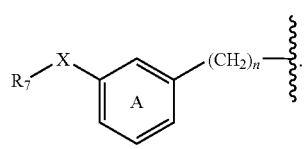

(II)

Ring A is substituted or unsubstituted; $R_7$ is an optionally substituted phenyl, optionally substituted furanyl, optionally substituted thienyl or optionally substituted pyridyl group; n is an integer from 1-4; and X is a bond, $CH_2$, $OCH_2$, $CH_2OC(O)$, CO, OC(O), C(O)O, O, S, SO or $SO_2$. Examples of suitable substituents for Ring A and the aryl groups represented by $R_7$ are provided in section above describing suitable aryl group substituents.

j) $R_3$ is represented by Formula (II), wherein Ring A is substituted or unsubstituted; $R_7$ is an optionally substituted phenyl group; n is 1; and X is CO.

k) $R_3$ is represented by Formula (II), Ring A is unsubstituted $R_7$ is an optionally substituted phenyl group; n is 1; and X is CO. More preferably, $R_7$ is a phenyl group.

l) $R_4$ is an optionally substituted aryl group, an optionally substituted cycloalkyl group, an optionally substituted $C_1$-$C_4$ aralkyl group or an optionally substituted $C_1$-$C_4$ cycloalkylalkyl group.

m) $R_4$ is an optionally substituted phenyl group, an optionally substituted phenyl-$C_1$-$C_4$-alkyl group, an optionally substituted diphenyl-$C_1$-$C_4$-alkyl group, an optionally substituted $C_3$-$C_8$-cycloalkyl-$C_1$-$C_4$-alkyl group or an optionally substituted di-($C_3$-$C_8$-cycloalkyl)-$C_1$-$C_4$-alkyl group.

n) $R_4$ is an optionally substituted benzyl, an optionally substituted diphenylmethyl, an optionally substituted 2-phenylethyl, an optionally substituted 1,2-diphenylethyl, an optionally substituted 2,2-diphenylethyl or an optionally substituted 3,3-diphenylpropyl. Preferred substituents for these values of $R_4$ include $C_1$-$C_4$ alkyl, $C_1$-$C_4$ alkoxy, halogen, CN, $C_1$-$C_4$-alkylthiol, $C_1$-$C_4$-haloalkyl and phenoxy.

In another preferred embodiment, the compound of Formula (I) is characterized by one or more of Features a), f) and l), and preferably all of Features a), f) and l).

In another preferred embodiment, the compound of Formula (I) is characterized by one or more of Features b), h) and m), and preferably all of Features b), h) and m). More preferably, the compound of Formula (I) is additionally characterized by Feature d).

In another preferred embodiment, the compound of Formula (I) is characterized by one or more of Features b), d), i) and m), and preferably all of Features b), d), i) and m). Alternatively, Feature m) is replaced by Feature n). In another alternative, Feature m) is replaced by Feature n) and Feature i) is replaced by Feature j).

In another preferred embodiment, the compound of Formula (I) is characterized by one or more of Features b), d), k) and m), and preferably all of Features b), d), k) and m).

In yet another embodiment, the method of the present invention is carried out with the compound of Formula (III) in place of the compound of Formula (I):

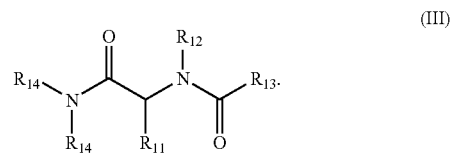

(III)

$R_{11}$ is —H, a substituted or unsubstituted aryl, a substituted or unsubstituted aralkyl, a substituted or unsubstituted heteroaryl or a substituted or unsubstituted heteroaralkyl;

$R_{12}$ is alkyl substituted with $NR_{15}R_{16}$, a substituted or unsubstituted aryl, a substituted or unsubstituted heteroaralkyl, or a substituted or unsubstituted heterocycloalkylalkyl;

$R_{13}$ is a substituted or unsubstituted alkyl, a substituted or unsubstituted aryl, a substituted or unsubstituted aralkyl, a substituted or unsubstituted cycloalkylalkyl, a substituted or unsubstituted heteroaryl, a substituted or unsubstituted heteroaralkyl, a substituted or unsubstituted benzophenonyl, or a substituted or unsubstituted cycloalkylalkyl; and each $R_{14}$ is independently, —H, a substituted or unsubstituted alkyl, a substituted or unsubstituted aryl, substituted or unsubstituted aralkyl or a substituted or unsubstituted heteroaralkyl;

$R_{15}$ and $R_{16}$ are independently selected from H, a substituted or unsubstituted alkyl, a substituted or unsubstituted cycloalkyl, a substituted or unsubstituted aryl or unsubstituted aralkyl or $R_{15}$ and $R_{16}$ together with the nitrogen to which they are attached are a heterocycloalkyl.

The invention is illustrated by the following examples, which are not intended to be limiting in any way.

EXEMPLIFICATION

Example 1

Suppression of Chronic Transplant Rejection Using Compound 1 in a First Mouse Model The ability of Compound 1 to inhibit chronic transplant rejection in a mouse model was tested. Specifically, hearts from donor B6.C-$H2^{bm12}$ mice were transplanted into C57/BL6 recipient mice (MHC II mismatch) using standard protocol described in Hancock, W. W., et al. *Proc. Natl. Acad. Sci. USA* 93: 13967 (1996) and Yuan et al., *Transplantation* 73:1736, the entire teachings of which are incorporated herein by reference. Following surgery, the mice were divided into the following treatment groups with seven mice each:

Group I was a control group that was untreated.

Group II was treated with Compound 1 at a dose of 75 mg/kg/day subcutaneously for fourteen days following surgery.

At eight weeks following transplant surgery, the mice were sacrificed and evaluated for chronic rejection accelerated atherosclerosis. Briefly, transplanted hearts were fixed in formalin, embedded in paraffin and sectioned coronally. The sections were scanned for arterial blood vessels, which were subjected to a histopathological score. The histopathological scores (range 0-5 indicating severity of chronic rejection accelerated atherosclerosis, with 0 being normal blood vessel and 5 being fully occluded) are shown in FIG. 1. Compound 1 significantly (p=0.0002) prevented histological evidence of chronic rejection when data was averaged for all animals in the study. The effect was even more significant when the score for each animal is examined individually, e.g., 4/7 animals were free of vasculopathy, while three treated animals showed full involvement. The three animals in the treatment group showing the higher scores were the last to be treated, and they may have suffered from diminished exposure to the compound, which was observed to have precipitated from solution during handling and dilution in the syringe when they were being treated. It is likely that increased bioavailability resulting from improved compound formulation will result in more complete protection from chronic rejection vasculopathy.

Example 2

Figure 2:
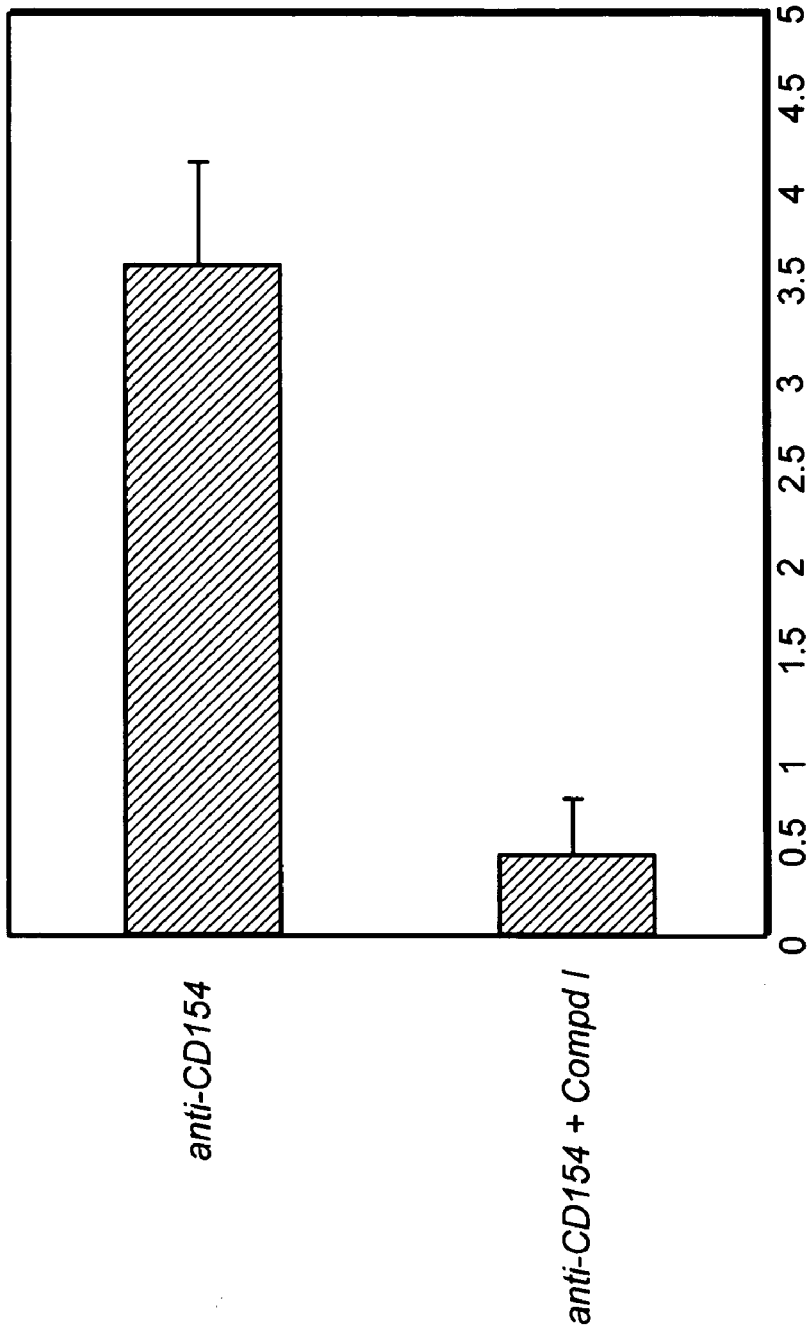
FIG. 2 is a graph showing inhibition of chronic vasculopathy in transplanted hearts in a model consisting of only fully mismatched mice greater than 100 days following heart transplant. The graph compares inhibition of chronic vasculopathy in a group of mice treated with a single 250 μg dose of anti-CD154 monoclonal antibody immediately following heart transplant surgery with a group of mice treated with a single 250 μg dose of anti-CD154 immediately following heart transplant surgery and 75 mg/kg of Compound 1 subcutaneously for fourteen days after heart transplant surgery. The scores shown in the graph range from zero to five to indicate the severity of chronic rejection accelerated atherosclerosis, with zero being normal blood vessel and five being fully occluded.

Suppression of Chronic Transplant Rejection Using Compound 1 in a Second Mouse Model The ability of compound 1 to inhibit chronic transplant rejection was tested in a mouse heterotypic allogeneic heart transplant model in which acute allograft rejection was prevented with CD154 blockade as previously described (Hancock, W. W. et al. 1996. *Proc. Natl. Acad. Sci. USA.* 93:13967; and Yuan et al., *Transplantation* 73:1736). Briefly, this model consists of fully mismatched cardiac allografts (C57/BL 6 donor with Balb/C recipient). Acute rejection occurred in all transplant recipients within 10 days post surgery without treatment, while treatment with Compound 1 alone resulted in a statistically significant extension in transplant survival to about 20 days. A third group in which acute rejection is blocked by administering a single 250 μg dose of anti-CD154 (anti-CD40 ligand) monoclonal antibody was established, and acute rejection (as evidenced by cessation of contraction of the transplanted heart) occurred in approximately 50% of recipient animals. Importantly, the remaining 50% of recipients that did not demonstrate acute rejection retained a finctional graft for an extended period of time (greater than 100 days). Histological examination of the transplanted hearts in this treatment group at 100 days post surgery displays 3 major hallmarks of the chronic rejection process. These include profound athlerosclerotic blockages of heart arteries, cellular inflammation (immune cell infiltration into the heart muscle itself), and fibrotic scarring of the cardiac parenchyma. The hearts were subjected to a histopathological score. The histopathological scores (range 0-5 indicating severity of chronic rejection accelerated atherosclerosis, with 0 being normal blood vessel and 5 being fully occluded) are shown in FIG. 2. Thus the addition of anti-CD154 to this model offers certain similarities to the human transplant clinical condition in that acute rejection is managed (in this case with the anti-CD154 monoclonal antibody) so that chronic rejection pathology can be observed. The addition of Compound 1 (75 mg/kg daily, subcutaneous for 14 days post surgery) to a second group of animals that had received anti-CD154 (to block acute rejection given as a single dose at immediately following surgery) resulted in a striking lack of acute rejection in 100% of transplant recipient animals for more than 100 days post surgery. Histological evaluation of the transplanted hearts for all three indicators of chronic graft rejection described above revealed a dramatic inhibition of all indicators of chronic rejection of the transplant. Histopathological scores for these hearts are also shown in FIG. 2. Comparison of the scores in FIG. 2 show that animals treated with Compound 1 had a dramatic decrease in chronic rejection compared with animals that were not treated with Compound 1.

Example 3

Suppression of Transplant Rejection Using Compound 1

The ability of Compound 1 to inhibit transplant rejection in a mouse model was tested. Specifically, the heart from C57/BL6 mice was transplanted into Balb/c recipient mice (total MHC mismatch) using standard protocol described in Hancock, W. W., et al. "Costimulatory function and expression of CD40 ligand, CD80 and CD86 in vascularized murine cardiac allograft rejection" *Proc. Natl. Acad. Sci. USA* 93: 13967 (1996). Following surgery, the mice were divided into the following treatment groups:

Group I is a control group that was untreated.

Group II was treated with Compound 1 at a dose of 75 mg/kg/day subcutaneously for fourteen days following surgery.

Control mice receiving no treatment reproducibly experienced rejection of their transplanted hearts after only ten days. Mice receiving Compound 1 alone showed a statistically significant delay (two to three weeks) (p<0.001) in the onset of rejection.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting chronic rejection of a transplanted organ or transplanted tissue in a human in need thereof, wherein the transplanted organ or transplanted tissue is heart, kidney, lung, liver, pancreas, pancreatic islets, brain tissue, stomach, large intestine, small intestine, cornea, skin, trachea, muscle or bladder, said method comprising the step of administering an effective amount of a compound represented by the following structural formula:

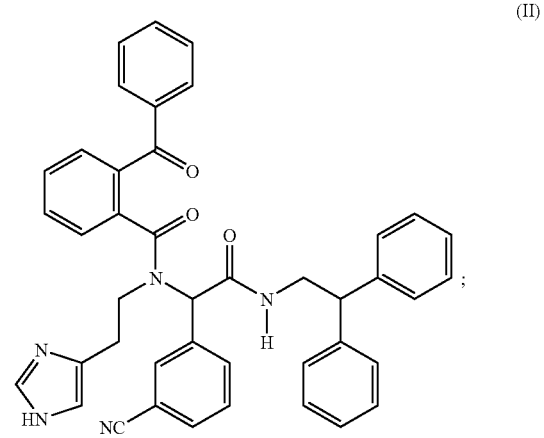

(II)

or a pharmaceutically acceptable salt thereof.

* * * * *